United States Patent [19]

Nady-Mohamed

[11] Patent Number: 5,353,784
[45] Date of Patent: Oct. 11, 1994

[54] ENDOSCOPIC DEVICE AND METHOD OF USE

[75] Inventor: Nady E. Nady-Mohamed, Williamsville, N.Y.

[73] Assignee: The Research Foundation of Suny, Albany, N.Y.

[21] Appl. No.: 42,295

[22] Filed: Apr. 2, 1993

[51] Int. Cl.⁵ ............................................. A61B 17/02
[52] U.S. Cl. ...................... 128/20; 604/106; 606/119; 606/198
[58] Field of Search .............................. 128/17, 20, 18; 606/119, 191, 198, 206–208; 604/104–109

[56] References Cited

U.S. PATENT DOCUMENTS

| | | | |
|---|---|---|---|
| 4,559,944 | 12/1985 | Jaeger | 128/344 |
| 4,873,978 | 10/1989 | Ginsburg | 606/198 |
| 4,909,789 | 3/1990 | Taguchi et al. | 606/198 X |
| 5,074,867 | 12/1991 | Wilk | 606/128 |
| 5,176,128 | 1/1993 | Andrese | 128/20 |
| 5,178,133 | 1/1993 | Pena | 128/20 |
| 5,195,506 | 3/1993 | Hulfish | 606/198 X |
| 5,195,507 | 3/1993 | Bilweis | 128/20 |
| 5,235,966 | 8/1993 | Jamner | 606/198 X |

FOREIGN PATENT DOCUMENTS 2739589  3/1979  Fed. Rep. of Germany ...... 606/119

Primary Examiner—Richard J. Apley
Assistant Examiner—Donna L. Maraglio
Attorney, Agent, or Firm—Ronald Coslick

[57] ABSTRACT

A device useful in endoscopic and other surgical procedures is disclosed. Two arms supporting a membrane therebetween are extendible from within a tube to an operative shape in which the arms diverge and spread the membrane between them. The device may be used for retraction or shielding, and is further provided with means for facilitating aspiration or irrigation. Related methods are also disclosed.

8 Claims, 5 Drawing Sheets

ENDOSCOPIC DEVICE AND METHOD OF USE

BACKGROUND OF THE INVENTION

1. Field of the Invention

This invention relates generally to devices useful in endoscopic diagnostic and surgical procedures, and more specifically to barrier-forming or shielding means insertable into a cavity within the body through a small incision or other aperture, and methods of using the same.

2. Brief Description of the Prior Art

The endoscope is a narrow tubular device having optical transmission capabilities which is inserted through a small incision or other aperture into a cavity within the body to facilitate inspection of the interior of the cavity. Endoscopic diagnosis and surgery are performed by using an endoscope in conjunction with other instruments which are designed to perform typical diagnostic or surgical functions, but which have been adapted for insertion through other nearby apertures. These devices typically comprise a long narrow tube, with an operative mechanism, such as scissors, forceps, or a clamp, situated at the distal end of the tube and connected by some connecting means disposed within the tube to a manual actuation means situated at the proximal end. Use of these devices has the advantage of lessening the trauma which is necessarily experienced by a patient in the course of a surgical procedure, thereby reducing risk, pain, recovery time, and costs.

Within the field of endoscopic diagnosis and surgery, there has been a long-felt need for a barrier-forming device which is insertable through a small incision or other aperture but which can be subsequently expanded to occupy a much greater planar area. Such a device has applications in retraction of tissues to prevent them from obstructing the work of other instruments, in providing shielding for sensitive tissues and organs from the damaging effects of laser surgery or radiation therapy, or in providing a grasping means useful for engaging and holding an organ such as the uterus by walls of its lumen, without engaging or otherwise disturbing the tissue on the outside of the organ. While there are several patents disclosing devices which address these needs, to date they remain either unfulfilled or only partially fulfilled by the existing prior art.

U.S. Pat. No. 5,178,133, issued Jan. 12, 1993 to Pena, discloses a laparoscopic retractor device having two rigid arms supporting a membrane which are disposed within a tube and are activated by a plunger. In this device the arms unfold in opposing directions through pivotal rotation at the end of the tube. A membrane, consisting of a tubular latex sheath having an open and a closed end, is disposed about the arms while they are in their folded position, and is expanded by the arms when they are spread apart. The device requires a biasing force to expand the arms and retain their position relative to one another against the elastic force of the membrane.

U.S. Pat. No. 5,176,128, issued Jan. 5, 1993 to Andrese, teaches an organ retractor comprising a pair of flexible arms formed in their operative extended shapes which are deformed and disposed within an introducer having an oblong cross section and containing separate apertures for each arm and a plunger mechanism. Upon expulsion from the introducer, the arms radiate in opposing directions, and filaments disposed between the arms and affixed to the plunger mechanism provide some reinforcement for maintaining their proper orientation. The device cannot provide a solid barrier for purposes of either retraction or shielding.

U.S. Pat. No. 5,074,867, issued Dec. 24, 1991 to Wilk, teaches a membrane disposed within a tube which is ejected upon insertion of the tube into a body cavity and partially expanded by elongate members. The membrane must subsequently be fully expanded and oriented about the area to be shielded through the use of laparoscopic forceps.

U.S. Pat. No. 4,559,944, issued Dec. 24, 1985 to Jaeger, teaches surgical forceps having two arms of unequal length, wherein the longer of the two arms is insertable through the cervix into the uterus, while the shorter arm is shaped to grip the outside of the cervix by capturing it between the arms. The longer arm is further provided with a longitudinal bore, and is tipped with an inflatable membrane which, when inflated, engages the walls of the lumen of the uterus, thereby providing a measure of control of the positioning of the uterus. The device cannot accomplish gripping or manipulation of the uterus or cervix without engagement of the outer surface of the cervix.

SUMMARY OF THE INVENTION

The present invention is distinguished over the prior art, and over the foregoing patents in particular, in that it provides a barrier-forming device having two flexible arms disposed within a single aperture within a tube, which, when in operation, expand a membrane fixed between them to its operative position through return to their preformed shapes, and which will maintain either their retracted or extended positions without the need for an additional biasing force. Further, the present invention provides an endoscopic shielding means which is fully expandable to its operative position without the need for the use of additional devices. In addition, the present invention provides an expandable device useful for gripping or manipulating a uterus or other similar organ within the body through engagement of the walls of the lumen of the organ, without engaging the outer surface of the same.

It is therefore an object of the present invention to provide a new and improved remotely expandable barrier-forming device for use in endoscopic surgery.

It is a further object of this invention to provide an endoscopic retractor which can be inserted into a cavity within the body through a small incision or other aperture and subsequently expanded through remote means.

It is a further object of this invention to provide an endoscopic retractor which will maintain either an extended or a retracted position without the need for additional biasing means.

It is a further object of this invention to provide an endoscopic retractor which includes means for irrigation or aspiration of the area in which it is deployed, It is a further object of this invention to provide an endoscopic barrier-forming mechanism which will shield an organ or tissue from the effects of either radioactive or laser emissions.

It is a further object of this invention to provide an endoscopic method for shielding an organ or tissue from the effects of either radioactive or laser emissions.

It is a further object of the present invention to provide a remotely expandable barrier-forming device useful for engaging and grasping a uterus or other similar organ within the body without engaging the outer surface or damaging the lumen of the same.

It is a further object of the present invention to provide a method for engaging and grasping a uterus or other organ within the body without engaging the outer surface or damaging the lumen of the same.

DESCRIPTION OF THE PREFERRED EMBODIMENT

Figure 1:
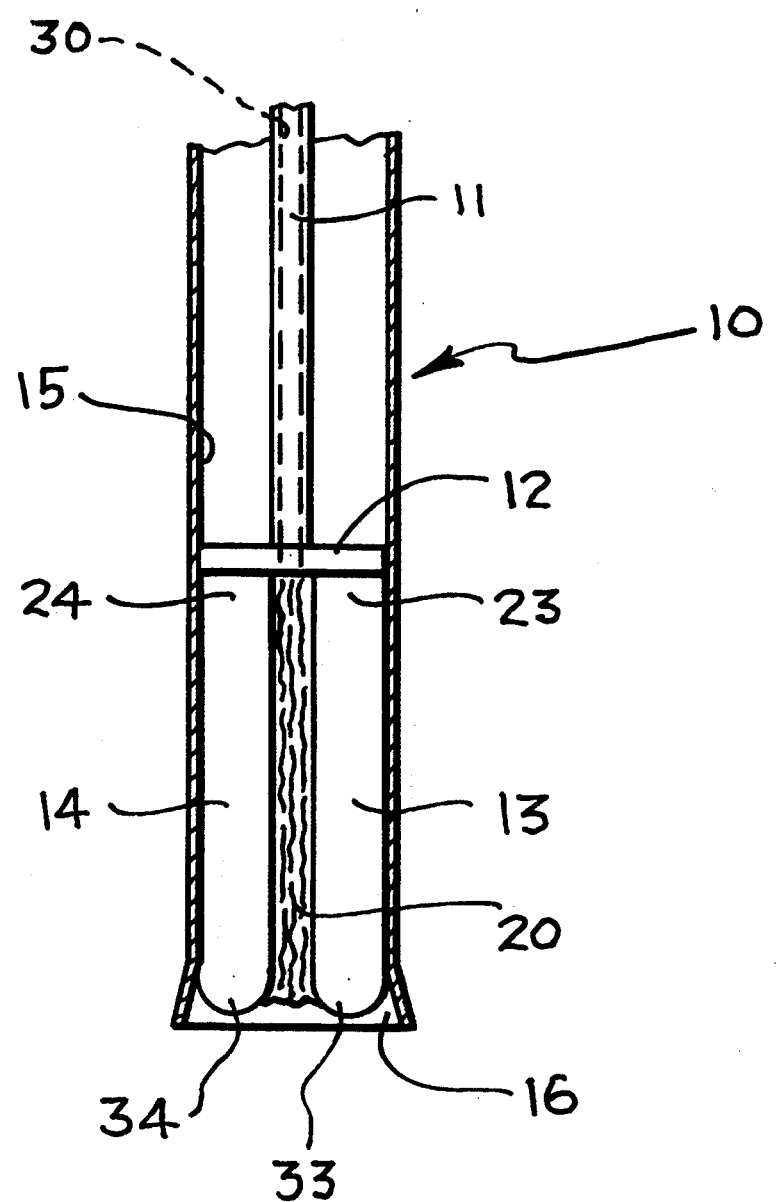
FIG. 1 is a longitudinal cross section of the distal end of the remotely expandable barrier-forming apparatus showing a hollow plunger means, a pair of flexible arms, and a membrane, slidably disposed within a tube.

Referring to the drawings as enumerated above, there is shown in FIG. 1 a cylindrical tube 10 within which is slidably disposed a plunger 11. The plunger 11 passes through a disc 12, and is fixed to the disc such that any longitudinal movement of the plunger within the tube is also imparted to the disc. Flexible arms 13 and 14 are also fixed, at their proximal ends 23 and 24, to the disc 12. The arms are generally cylindrical with rounded ends 33 and 34, and may have a circular cross-section or may have a crescent cross-section to facilitate storage of a membrane between them, as is described below.

The flexible arms 13 and 14, being preformed to their operative extended shape, are deformed when in the retracted position, and are therefore in frictional contact with the inner surface 15 of the tube 10. As a result of this friction the arms will maintain their retracted position without the need for an additional biasing force on the plunger. The arms may be formed of any suitable resilient material such as rubber or spring steel. The tube 10 is provided at its distal end with a flanged opening 16, and is of a sufficiently small diameter for use in endoscopic procedures, which typically require diameters of approximately 10 millimeters.

Figure 2:
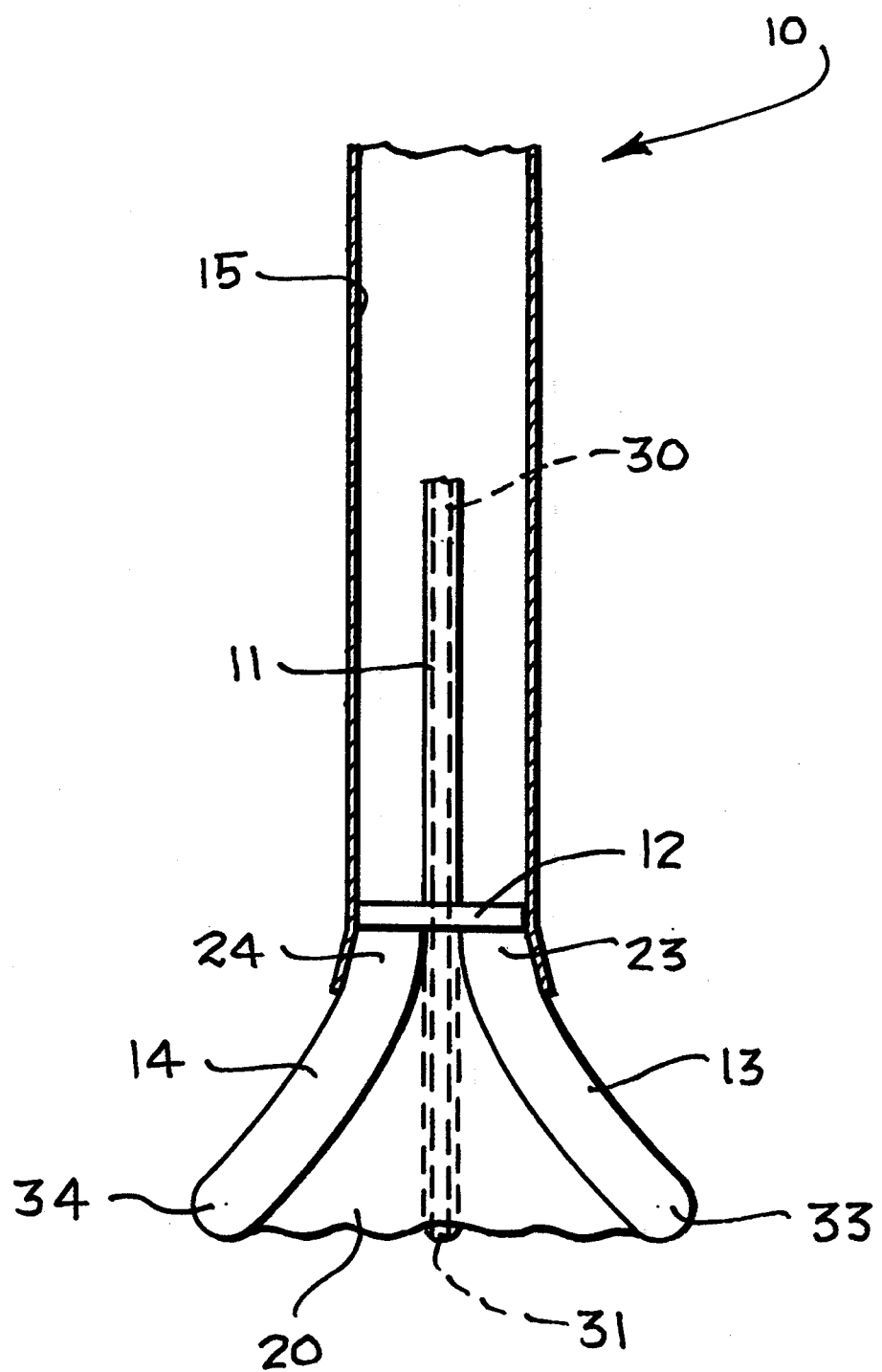
FIG. 2 is a longitudinal cross section of the distal end of the remotely expandable barrier-forming apparatus showing the plunger and arms in an extended position, with a membrane spread between the arms.
Figure 3:
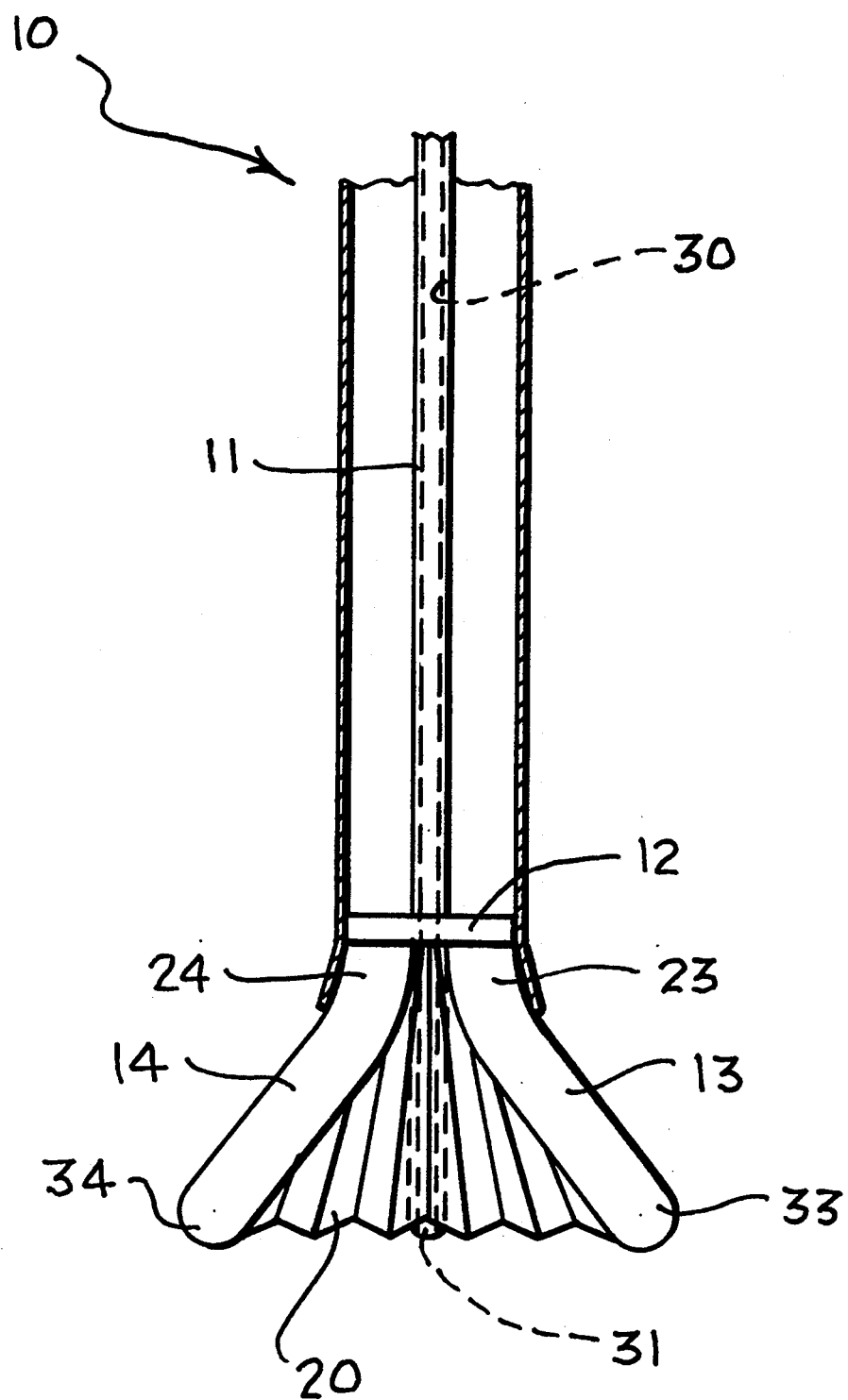
FIG. 3 is a cross section of the distal end of the barrier-forming apparatus showing the plunger and arms in an extended position, with a membrane spread between them which is provided with pleats.

A membrane 20 is disposed between the arms 13 and 14, and is fixed to each arm along the lengths of its outer edges. In the retracted position, as illustrated in FIG. 1, the membrane 20 is folded or otherwise compressed for storage between the arms. In the extended position, as illustrated in FIGS. 2 and 3, the previously deformed arms 13 and 14 attain their natural shape, and membrane 20 is thereby spread to occupy the space between them. FIG. 2 shows a membrane 20 in its expanded position, with the plunger lying behind the membrane, while FIG. 3 shows an expanded membrane 20 which is provided with pleats to better facilitate the folding and unfolding process undergone during extension and retraction. The plunger is provided with a longitudinal bore 30 and an open distal end 31, which facilitate the insertion through or attachment to the plunger of a tube or other means to effect aspiration or irrigation at said open distal end 31. The open end may be situated on the disc 12, or the plunger may extend between the arms, such as is illustrated in FIGS. 2 and 3. To minimize the risk of trauma to a patient when the apparatus is in use, as described below, the plunger should in no case extend beyond the extent of the membrane in its extended position.

As a result of their inherent bias toward their preformed shapes, the arms will maintain the extended position without need for any additional biasing force. The lengths of the arms, the angles at which they diverge from the longitudinal axis of the tube, and the consequent size and area of the membrane may be varied depending upon the particular application of the device. For example, a device intended for insertion within the uterus would have arms of sufficient length to firmly engage the walls of the lumen of the uterus without the risk of tearing or other damage to the tissue. This would require arms with lengths of approximately 6 to 8 cm., which diverge from the longitudinal axis of the tube such that the angle between them is approximately 30 degrees.

The material of which the membrane is comprised may vary depending upon the application. For simple retraction, any pliable, non-toxic material will suffice. For shielding during laser surgery, a dark and preferably black material is required. For shielding during radiation therapy, a radio-opaque material is required.

Figure 4:
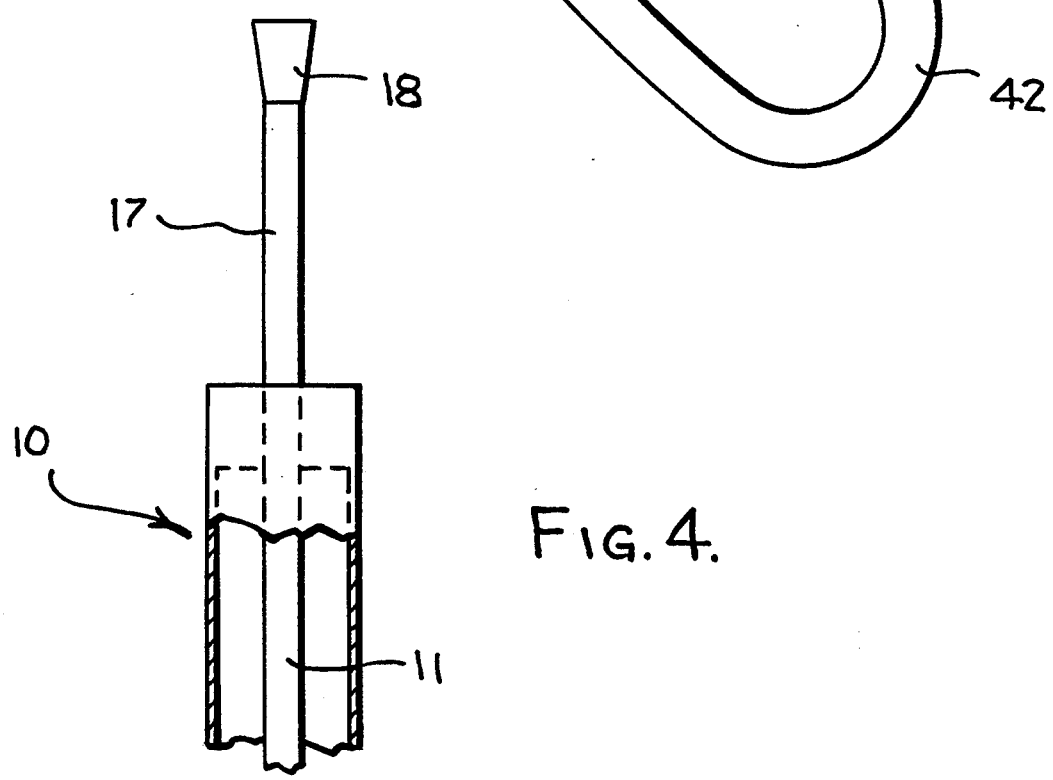
FIG. 4 is a partial cross section of the proximal end of the barrier-forming apparatus showing the hollow plunger disposed within and extending from the proximal end of the tube.

The plunger 11 extends through the length of the tube 10 and outward from the tube at its proximal end 17, as shown in FIG. 4, terminating in a flanged end piece 18 which facilitates the insertion of a conventional tube (not shown) or similar means to achieve aspiration or irrigation at the plunger's distal end. In other analogous embodiments, this end piece may comprise coupling means for the direct attachment of a tube or hose for the same purposes.

Figure 5:
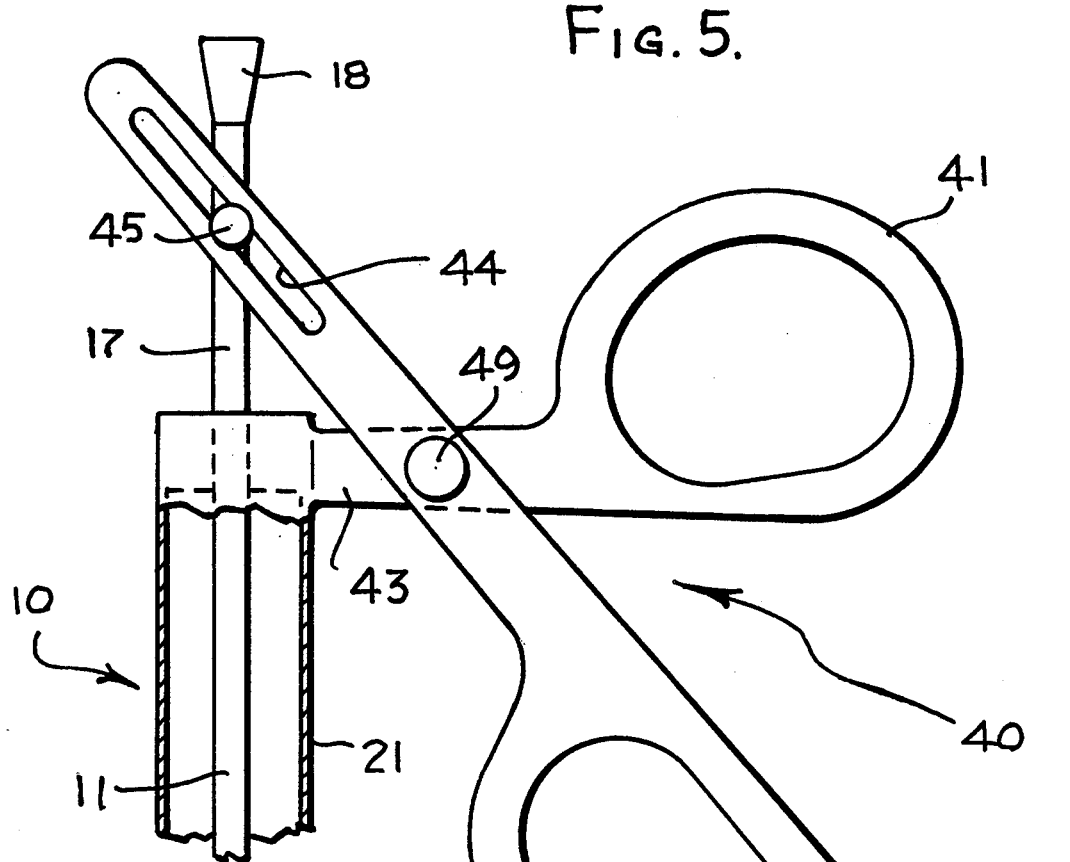
FIG. 5 is a partial cross section of the proximal end of the barrier-forming mechanism showing a scissors-like actuation means for slidably moving the plunger within the tube.

The plunger 11 is slidably disposed within the tube 10, and the arms and membrane are expelled from the distal end of the tube or withdrawn into the tube by sliding the plunger in the desired direction. This may be accomplished by simply gripping the plunger at its proximal end and pushing or pulling it. FIG. 5 illustrates a preferred embodiment, comprising a scissors-like mechanism 40 having scissor arms 41 and 42 which are pivotally attached near their midpoints with a rivet 49 or other similar pivotal attachment means. A first scissor arm 41 is fixed at its distal end 43 to the outer surface 21 of the tube, while a second longer scissor arm 42 having a longitudinal aperture 44 is coupled to a coupling means 45 affixed to the plunger. When the finger rings of the scissor arms 41 and 42 are brought together, the coupling means 45 is caused to slide within the longitudinal aperture 44, thereby causing the plunger 11 to be moved toward the distal end of the tube. Similarly, separation of the scissor arms causes movement of the plunger toward the proximal end of the tube. Equivalent embodiments of this concept may be similarly employed, such as one in which the fixed and slidable connections of the scissor arms are reversed such that the tube is slidable over the plunger and arms, rather than the plunger being slidable within the tube. Other means may be similarly employed to facilitate extension and retraction of the arms and membrane.

Figure 6:
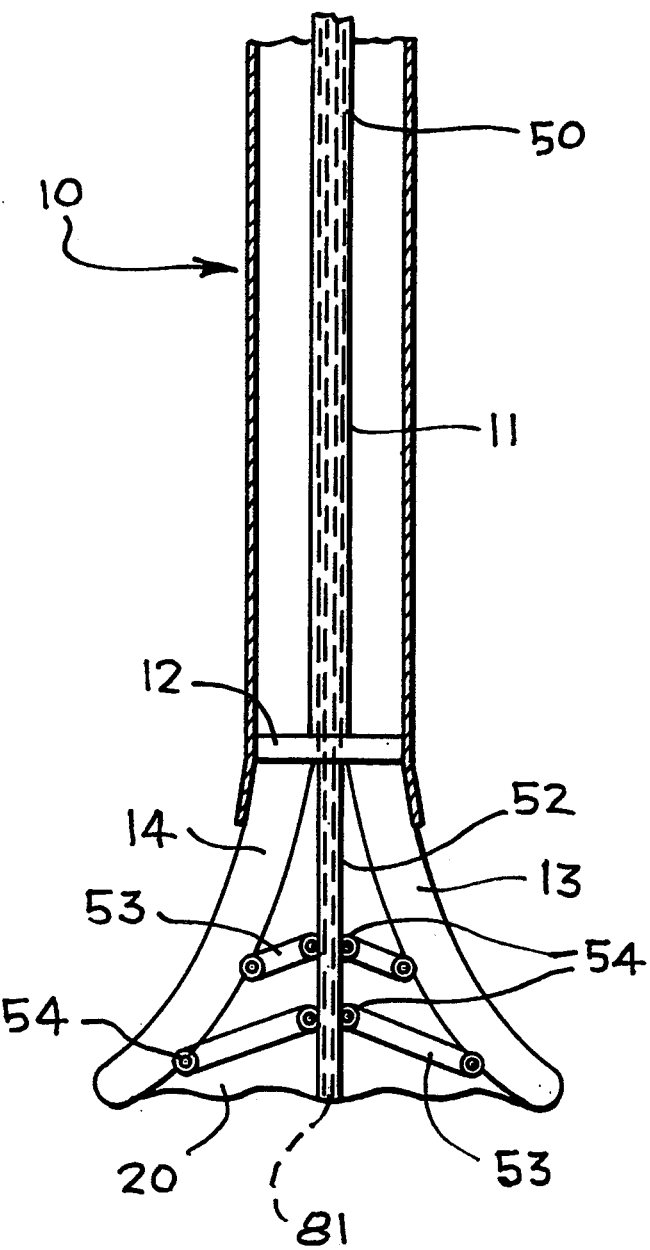
FIG. 6 is a longitudinal cross section of an alternative embodiment, showing the tube with the membrane in the extended position, including a rod, having a longitudinal bore, slidably disposed within the plunger, and a plurality of ribs disposed between the rod and the arms, for adding rigidity to the arms in said position.
Figure 7:
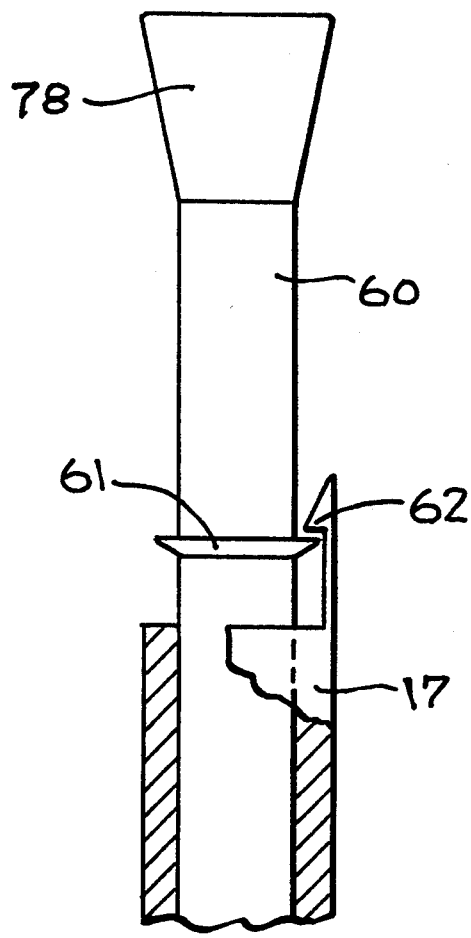
FIG. 7 is a cross section of the proximal end of the apparatus in an alternative embodiment, showing the proximal end of the plunger with a rod, having a longitudinal bore, slidably disposed therein, and means for locking the second tube in a forwardly extended position.

A further embodiment of the invention, which provides for added rigidity of the arms in their extended position, is illustrated in FIGS. 6 and 7. FIG. 6 shows the apparatus, wherein the plunger 11, which terminates at the disc 12, is provided with a longitudinal bore, within which is slidably disposed a rod 50 having a longitudinal bore and an open distal end 81. The rod near its distal end 52 is provided with a plurality of rigid ribs 53 which are pivotally joined to the outer surface of the rod at pivotal joints 54. The ribs extend laterally from the rod and are pivotally joined at their opposite ends to the arms 13 and 14, such that, when the arms are urged by the plunger to their extended position, the rod is drawn forward with the arms, and the ribs are spread by the expansion of the arms.

Near its proximal end 60, the rod is provided with an annular ring 61 about its circumference, as illustrated in FIG. 7. The rod is also provided at its proximal end with an end piece 78 to facilitate aspiration or irrigation, as in other embodiments previously described.

When the apparatus is in the extended position, the annular ring 61 is engaged by a lip 62 which extends rearward from the proximal end of the plunger 17, such that, when engaged as such, movement of the rod toward the proximal end of the apparatus is prevented. This in turn prevents collapse of the arms and membrane toward the rod due to the rigid ribs which join the arms and the rod. The locking feature is of critical importance in applications in which it is necessary for the arms to resist a collapsing force, such as in the laparoscope assisted vaginal hysterectomy procedure described below.

OPERATION AND METHODS OF USE

While simple operation of the device heretofore described should be apparent, particular applications will be described.

For use as a retractor or shield, the disclosed device is inserted through an aperture, such as an endoscopic tube which is fitted into a small incision, into a body cavity such as the peritoneal cavity. Upon insertion, the distal end of the tube is placed in the vicinity of the organ or tissue of interest, and the membrane and arms are extended from within the tube, thereby forming a solid barrier for shielding or retraction of the organ. This application is useful, for example, for shielding a delicate organ such as an ovary from stray bursts of laser light during laser surgery, or for shielding tissue which is apart from a target area from stray radiation during radiation therapy. Subsequent to use the arms and membrane are withdrawn back into the tube and the device is withdrawn from the body.

In a second application, the device may be used for gripping and manipulation of the uterus and cervix. In this application the distal end of the tube is inserted through the cervix and into the uterus, whereupon the arms and membrane are extended from within the tube. Upon full deployment the arms and membrane will firmly engage the walls of the lumen.

This application of the apparatus is useful during the procedure of conization, wherein the cervix must be stabilized while cancerous tissue is removed by cutting a conical section of tissue from about the center of the cervix. Use of the disclosed apparatus to accomplish the necessary stabilization is preferable to use of the prior art devices in that it avoids the disturbance of cancerous tissues on the outer surface of the cervix because it cannot make inadvertent contact with those tissues. In addition, the single tube which extends outward from the cervix in this application causes less impedance to the cutting of the conical section than multi-armed prior art devices such as that disclosed in the Jaeger patent (described above).

This application of the apparatus is also useful in performing laparoscope assisted vaginal hysterectomy, wherein the uterus is engaged from within, and, subsequent to being freed from the surrounding tissue through surgical means, is withdrawn through the vaginal canal by withdrawing the device from the vaginal canal while it remains in its deployed state within the lumen. In this application, use of the embodiment of the apparatus which includes the stabilizing ribs is preferred. Withdrawal of the uterus requires a force of approximately 2 to 3 pounds, and due to the shape of the lumen of the uterus and the flexibility of the arms, the withdrawing force will be translated into a collapsing force upon the arms. Consequently, the reinforcing ribs and locking mechanism may be required to prevent deformation and slippage of the arms from within the lumen.

While this apparatus and various methods of its use have been shown completely in terms of particular embodiments and applications, one of ordinary skill in the art may generate additional embodiments and applications which do not depart from the spirit or exceed the scope of the claimed invention, and it should therefore be understood that within the scope of the claims the invention may be practiced otherwise than as specifically described.

What is claimed is:

1. A device for engaging the lumen of a patient's uterus, comprising:
   a tube, having a single longitudinal bore, for insertion through a patient's cervix into the uterus;
   arm means for engaging the uterus, said arm means including two opposing, flexible arms slidably disposed within the distal end of said tube, said arms being curved such that they diverge to attain a shape which generally conforms to the contours of the lumen of the uterus upon extension of said arms from within said tube;
   a plunger, provided with a longitudinal bore and open at both ends, and being slidably disposed within said tube and fixed near its distal end to said arms, for extending and retracting the arms relative to the distal end of said tube; within said tube, such that said arms and said membrane firmly engage the walls of the lumen of the uterus.

2. The apparatus of claim 1, wherein said rod is provided with a longitudinal bore and is opened at both ends.

3. The apparatus of claim 2, further comprising:
   tubular means in fluid communication with said rod, for providing aspiration or irrigation at the distal end of said rod.

4. The apparatus of claim 1, wherein said arm means further includes a membrane, disposed between said arms and fixed along its outer edges to said arms.

5. The apparatus of claim 4, wherein the membrane is provided with pleats.

6. The apparatus of claim 4, wherein said rod is coextensive at its distal end with said membrane.

7. A surgical method for engaging the lumen of the uterus while avoiding disturbance of the tissue on the outside of the uterus or the cervix, comprising:

providing an apparatus comprising two flexible curved arms supporting an expandable membrane and disposed within a tube, said tube being insertable into the uterus through the cervix, said arms and said membrane being extendable from within the tube to a deployed state in which said arms diverge in coplanar orientation from the longitudinal axis of said tube and expand said membrane therebetween so as to engage the lumen of the uterus, said arms being reinforced by ribs disposed between said arms and a rod slidably disposed within said tube;

inserting said tube into the uterus through the cervix; and deploying said arms and said membrane by causing them to be extended from within said tube, such that said arms and said membrane firmly engage the walls of the lumen of the uterus.

8. The method of claim 7, comprising further the step of withdrawing the uterus through the vaginal canal while maintaining the deployed state of the apparatus, subsequent to the uterus having been freed from surrounding tissues through a surgical procedure.

* * * * *